US005259844A

United States Patent [19]

Bilstad et al.

[11] Patent Number: 5,259,844

[45] Date of Patent: Nov. 9, 1993

[54] FLEXIBLE CONTAINER

[75] Inventors: Arnold C. Bilstad, Deerfield; Jerre T. Kachmar, Grayslake, both of Ill.

[73] Assignee: Clintec Nutrition Co., Deerfield, Ill.

[21] Appl. No.: 876,351

[22] Filed: Apr. 30, 1992

[51] Int. Cl.[5] .......... A61F 7/04

[52] U.S. Cl. .......... 604/403; 604/403

[58] Field of Search .......... 604/403, 408, 411, 415, 604/416; 215/DIG. 3

[56] References Cited

U.S. PATENT DOCUMENTS

| | | | |
|---|---|---|---|
| 2,104,031 | 1/1938 | Graber | 604/403 |
| 3,255,923 | 6/1966 | Soto | 604/411 X |
| 3,514,919 | 6/1970 | Ashton et al. . | |
| 3,554,256 | 1/1971 | Anderson . | |
| 4,072,233 | 2/1978 | Kramer et al. . | |
| 4,198,972 | 4/1980 | Herb | 604/408 |
| 4,519,184 | 5/1985 | Brunswick . | |
| 4,524,563 | 6/1985 | Sassi . | |
| 4,534,154 | 8/1985 | Gaubert . | |
| 4,598,529 | 7/1986 | Pongrass et al. . | |
| 4,609,369 | 9/1986 | Ball | 604/416 X |
| 4,636,412 | 1/1987 | Field | 604/408 |
| 4,840,017 | 6/1989 | Miller et al. . | |
| 5,088,994 | 2/1992 | Porat et al. | 604/403 X |
| 5,125,919 | 6/1992 | Miller et al. | 604/408 |

FOREIGN PATENT DOCUMENTS

| | | | |
|---|---|---|---|
| 91/11968 | 8/1991 | World Int. Prop. O. | 604/408 |

*Primary Examiner*—Robert A. Hafer
*Assistant Examiner*—Sam Rimell

[57] ABSTRACT

A container is provided for housing a fluid comprising a pair of flexible plastic walls, one of the plastic walls defining a front face and one of the plastic walls defining a back face. The plastic walls are secured together around a periphery thereof by a peripheral seal thereby defining an interior. An access member is located at an end of the container for allowing one to access a fluid contained within the interior. A fill port is located on a front face for allowing access to the interior of the container so that the interior can receive a fluid. The back and front face are sealed along a seal line located within the interior of the container in juxtaposition to the fill port. In an embodiment, the peripheral seal has a substantially Ω shape. A method for filling a container with fluid is also provided.

20 Claims, 2 Drawing Sheets

FLEXIBLE CONTAINER

BACKGROUND OF THE INVENTION

The present invention relates generally to flexible containers for housing liquid. More specifically, the present invention relates to containers that can be filled with a liquid under sterile conditions.

It is known to use flexible containers for housing parenteral and enteral solutions, such as liquid nutrients. Such containers should be manufactured and filled under sterile conditions to insure that they can be safely infused into patients.

In an article by I. M. Anderson entitled: Intasept—Aseptic Integrity in Bag-In-Box Packaging, Food Technology in Australia, Vol. 37 (9) September, 1985, pp. 399–401 a system is demonstrated for bag-in box packaging of liquids, and a machine for aseptic filling of such flexible, collapsible containers. As described in the article, a flexible, collapsible container, which comprises a pair of flexible plastic walls peripherally joined together, is filled through the use of a tubular port. The tubular port extends through one of the walls of the container to the container interior. The container includes spaced, outer and inner sealing diaphragms at either end of the tubular port. The outer diaphragm is outside of the walls of the container, and the inner diaphragm is inside the walls thereof.

The outer diaphragm is completely sealed to the tubular port about its periphery. But, the inner diaphragm is only spot sealed about its periphery so that fluid flow can take place across the inner diaphragm between the spot seals.

As described in the article, the flexible, collapsible container is connected to the Intasept filling machine. The outside of the tubular port is sterilized, and the container interior is typically already sterile. After sterilization, the outer membrane is penetrated, but not the inner membrane. The container is then filled through the tubular port with the desired amount of liquid, following which the inner membrane is welded in a continuous loop seal by welding which takes place through both walls of the container so that the container interior is sealed.

The disclosed bag system, and the method for filling and sealing it, has certain disadvantages. For example, a special laminated material must be used for the inner membrane, so that the inner membrane can be heat sealed to the tubular port, while the opposite container wall, through which the heat sealing process takes place, does not seal to the inner membrane. Additionally, the initial attachment of the intermittently sealed inner membrane is a matter of some complexity in the first place. Accordingly, the structure described in the Anderson article is difficult to make and costly.

U.S. Pat. No. 4,840,017, the disclosure of which is incorporated herein by reference, discloses a flexible, collapsible container that can be filled with conventional, aseptic filling machines, such as the Intasept machine, but which is a simpler structure, and which may be processed in a simpler manner to achieve the desired results of an aseptically sealed container for liquid materials with an improved seal.

To this end, the container comprises a pair of flexible plastic walls peripherally joined together. To fill the container, one connects a fluid conduit to a tubular port which communicates through one of the plastic walls to the container interior, thereby rupturing a sealed diaphragm that closes the bore of the tubular port. One then passes fluid through the conduit to fill the container, followed by sealing at least one wall of the tubular port and one plastic wall to the other plastic wall, forming a seal line that serves to close off flow communication between the tubular port and the portion of the container interior that contains the fluid. Thus, the container is sealed. In an embodiment, the seal line is a closed-loop seal that completely surrounds the bore to effectively block flow communications between the bore and the remaining portions of the container interior.

Although such a structure does provide a method for filling a container in a sterile manner, there may be disadvantages with such a container. In this regard, when the bore is sealed therearound by a closed-loop, after it has been filled with fluid, it has been found that the closed-loop seal acts as a stress concentrator. During shipping the container may fail due to the stresses that are exerted on the closed-loop seal.

A further problem that exacerbates the concentration of stress on the closed-loop seal is that the fact that the closed-loop seal is created after the container filling process. Therefore, residue such as oils from the liquid product that is housed in the container may still be on the interior of the flexible walls that are sealed together. This may result in a seal that cannot withstand the same stress that can be withstood by a seal created when the plastic is sealed in a dry state.

SUMMARY OF THE INVENTION

The present invention provides an improved container structure and method for filling same. Pursuant to the present invention, the container includes a seal line that is located in juxtaposition to a fill port. The seal line is preferably created when the flexible container is manufactured. Thereafter, when the container is filled and the opening of the fill port is sealed off, with a closed-loop seal, from the remaining interior of the container, the seal line functions to prevent a concentration of stress on the closed-loop seal. Accordingly, the incidence of failure of the closed-loop seal is greatly reduced.

To this end, a container is provided for housing a fluid comprising a pair of flexible plastic walls, one of the plastic walls defining a front face and one of the plastic walls defining a back face. The plastic walls are secured together around a periphery thereof by a peripheral seal thereby defining an interior. An access member is located at an end of the container for allowing one to access a fluid contained within the interior. A fill port is located on a front face for allowing access to the interior of the container so that the interior can receive a fluid. The back and front face are sealed along a seal line located within the interior of the container in juxtaposition to the fill port.

Preferably, the fill port includes a sealing diaphragm that is ruptured to provide access to the interior of the container.

In an embodiment, the seal line extends from a top of the peripheral seal in two lines to opposite sides of the peripheral seal.

In an embodiment, the peripheral seal has a substantially Ω shape.

In an embodiment, the seal line is defined, at least in part, by a pair of legs extending from a top of the peripheral seal, the legs defining an opening therebetween allowing fluid to flow from the fill port into a majority of the interior of the container. In a further embodiment, a further seal line is located between the legs and divides the opening into two openings.

The present invention also provides a method of filling with fluid a flexible, collapsible container which comprises a pair of flexible plastic walls peripherally joined together. The method comprises: providing on a face of the container a tubular port; creating a seal line extending from a top of the periphery of the walls to opposing sides thereof in juxtaposition to the tubular port; connecting a fluid conduit to the tubular port which communicates through one of the walls to the container interior; rupturing a sealing diaphragm that closes an opening of the tubular port and passing fluid through the conduit to fill the container; sealing at least one wall of the tubular port and one plastic wall to the other plastic wall with a closed-loop seal line that completely surrounds the opening, to block flow communication between the opening and most of the container interior, whereby the contents of the container remain sealed on disengagement of the fluid conduit from the tubular port; and cutting away at least portions of the other plastic wall situated in registry with the closed-loop seal line, whereby the resulting open port extending through the tubular port and container can serve as a hanger port.

Furthermore, an advantage of the present invention is that it provides an approximate two-fold increase in average burst pressure in test-to-failure over similar bags without a seal line.

An advantage of the present invention is that it provides a container that minimizes the force exerted on the back seal of the fill port whenever hydraulic or hydrostatics forces are applied.

Still further, an advantage of the present invention is that it provides a container having the ability to survive ASTM level II testing (simulated loose-load) with 0 defects as compared to greater than 10% failure rate for similar bags without a seal line.

Additionally, an advantage is that the seal line can be applied during the bag manufacturing operation with no additional piece part cost.

Moreover, an advantage of the present invention is that it allows the bag to hang evenly with a clearly definable meniscus.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
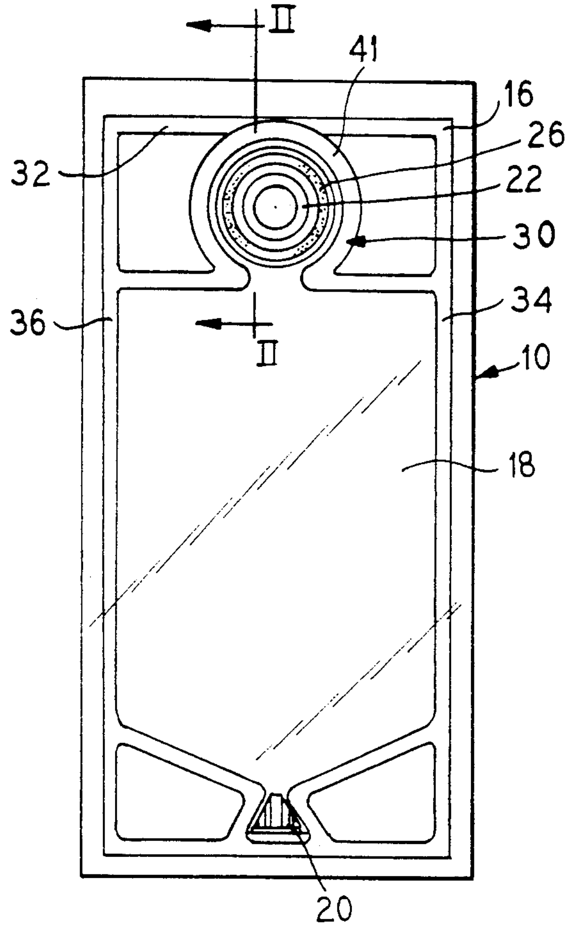
FIG. 1 illustrates a plan view of a flexible, collapsible container in a sealed configuration pursuant to the present invention.

The present invention provides an improved flexible, collapsible container. The container 10 comprises a pair of walls 12 and 14 which are joined together by a conventional, peripheral heat seal 16. The peripheral seal defines a sealed interior 18 within the container for housing a liquid. The container 10 is constructed so that it can be filled under sterile conditions.

A variety of materials can be used to construct the walls 12 and 14 of the container 10. For example, polyethylene, polypropylene, or the like can be used. In an embodiment that has been found to function satisfactorily, the walls 12 and 14 are constructed from a laminate comprising, from the outer layer in, nylon, EVOH, low density polyethylene. However, other materials can be utilized to construct the container 10 of the present invention.

Likewise, a variety of methods can be used to manufacture the container 10 of the present invention. For example, the container 10 can be constructed through a thermoforming process if desired. Likewise, the container 10 can be manufactured by simply heat sealing a pair of plastic sheets together.

As illustrated, the container 10 includes an access member 20 located at a bottom thereof. The access member 20 allows one to access the fluid contained within the container 10, with, for example, a spike or needle, so that the fluid can be administered to a patient. Of course, any access member 20 known in the art can be utilized. It has been found that an access member 20 such as that disclosed in U.S. patent application Ser. No. 604,338 entitled: "Wedge-Shaped Port for Flexible Containers", the disclosure of which is incorporated herein by reference, has been found to function satisfactorily in the container 10.

In order to fill the container 10, a fill port 22 is provided. The fill port 22 is designed to allow the container 10 to be filled with a liquid. For example, the fill port 22 can be constructed so that it will receive a fluid conduit coupler 23. An example of a fluid conduit coupler that can be used for an aseptic filling process is the Intasept aseptic bag-in-box filler.

Preferably, the fill port 22 includes a sealing diaphragm 24. The sealing diaphragm 24 is designed to be ruptured so that a fluid flow path is created between the fluid conduit coupler 23 of the filling machine and the interior 18 of the container 10.

Figure 2:
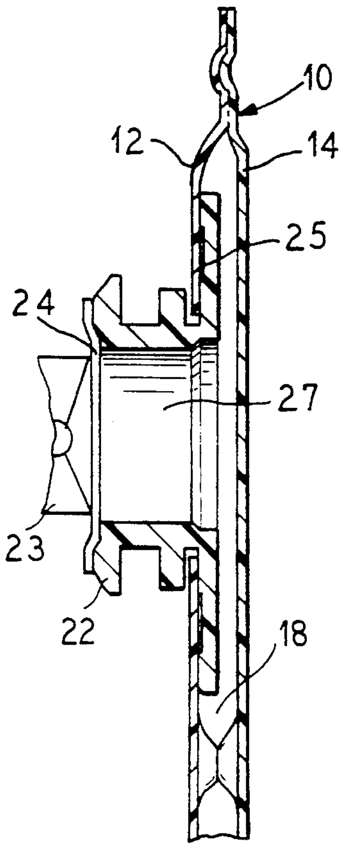
FIG. 2 illustrates a cross-sectional view of the container of FIG. 1 taken along lines II—II, however, during a step of the filling process.

After the container 10 is filled, as illustrated in FIG. 2, preferably, a heat seal is made between an angular flange 25 of the fill port 22 and the back wall 14 of the container 10 to form an annular, or closed-loop seal 26 that blocks flow communication between the opening 27 of the fill port and the majority of the interior 18 of the container 10. By this means, the fluid present in the interior 18 of the container 10 may be sealed under aseptic conditions. After the sealing process, the coupler 23 from an aseptic fill machine can be disconnected and the container 10 can be then transported to a customer.

Figure 3:
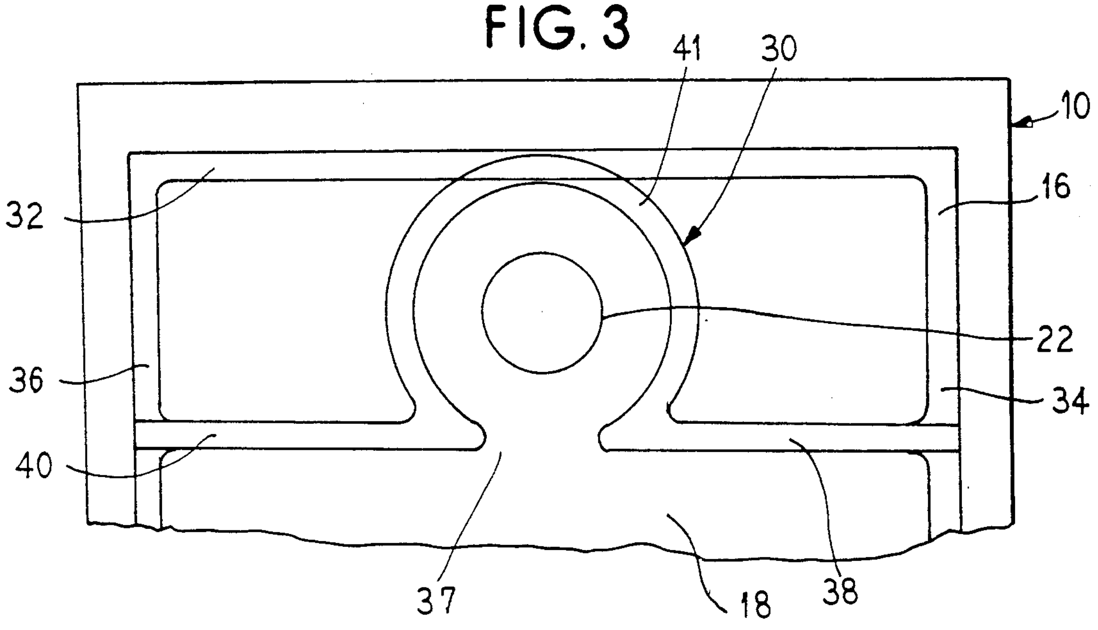
FIG. 3 illustrates an embodiment of the seal line of the container of the present invention.

As illustrated in FIGS. 1 and 3, the container 10 also includes a seal line 30 located within the interior 18 of the container 10 between the peripheral seals 16. With respect to FIG. 3, the container 10 is illustrated prior to the creation of the closed-loop seal. Preferably, the seal line 30 extends from a top seal 32 to opposite side seals 34 and 36 of the container 10. The seal line 30 is located in juxtaposition to the fill port 22. The seal line 30 is preferably created when the container 10 is created preferably by heat sealing the walls 12 and 14 together.

As illustrated, the seal line 30 is so constructed and arranged as to still allow fluid communication from the fill port 22 to substantially an entire interior 18 of the container 10. Fluid communication is thereby established through an opening 37 between two legs 38 and 40 defined by the seal line 30.

A variety of embodiments of the seal line 30 can be utilized. The seal line 30 affords protection while it includes an opening 37 that allows filling. The opening 37 of the seal line 30 is of sufficient size to allow normal filling of the container 10, yet not so wide as to lose the protective feature of the seal. The distance of the encircling seal portion 41 of the seal line 30 to the fill port 22 is small enough to afford protection from hydraulic and hydrostatic forces on the closed-loop seal 26, but large enough to allow for manufacturing tolerances.

The embodiment of the seal line 30 illustrated in FIGS. 1 and 3 has a substantially Ω like shape. The seal line 30 has been found to function satisfactorily and is presently preferred. In this regard, it has been found that by utilizing this seal line 30, after the fill port 22 is sealed with a closed-loop seal 26, to the back face 14 of the container 10, undue stress is not placed on this seal and the failure rate of the container is greatly reduced.

It should be noted that the seal line 30 is created when the plastic walls 12 and 14 are in a dry state. Therefore, the seal line 30 that is created is as strong as the heat sealability of the plastic material used to construct the container 10.

Figure 4:
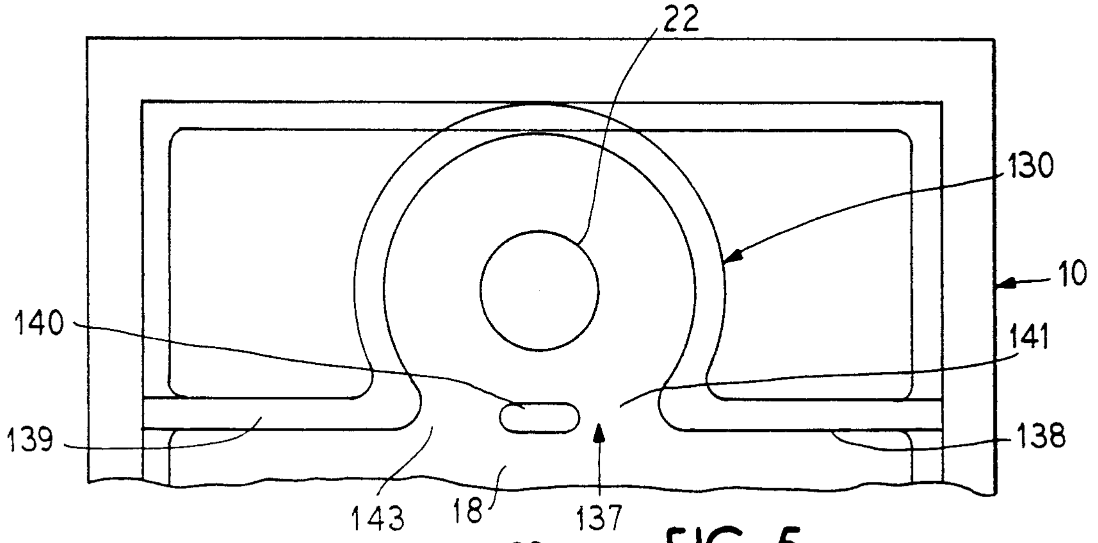
FIG. 4 illustrates a further embodiment of the seal line of the container of the present invention.

Referring now to FIG. 4 a further embodiment of the seal line 130 is illustrated. As illustrated, the seal line 130, although substantially Ω shaped, includes, within the opening 137 located between the legs 138 and 139, a small second seal line 140. The second seal line 140 effectively divides the opening 137 into two openings 141 and 143. The two openings 141 and 143 still allow fluid communication from the fill port 22 to the interior 18 of the container 10.

Figure 5:
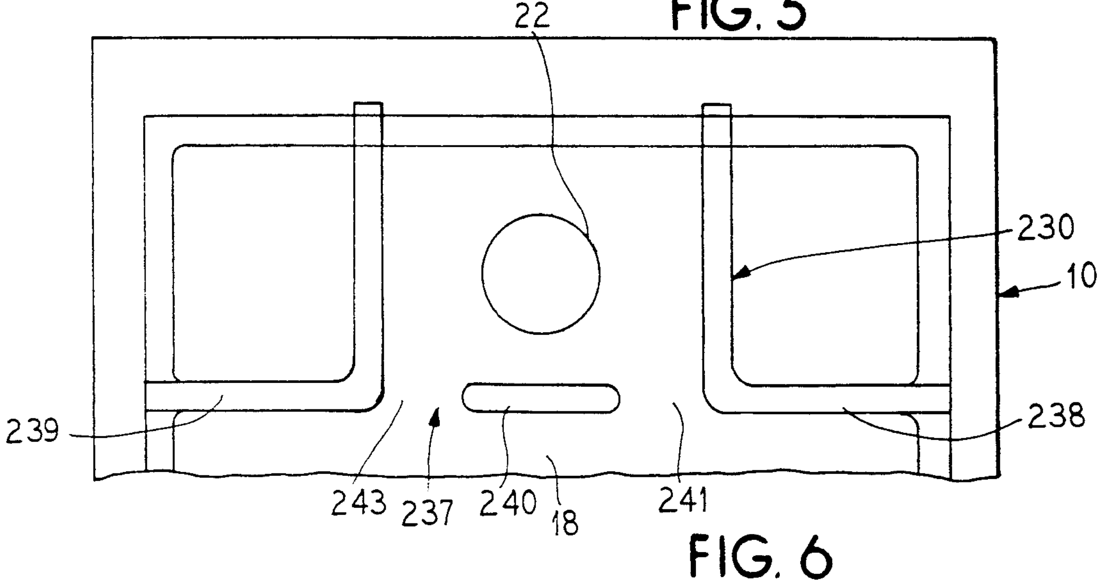
FIG. 5 illustrates a further embodiment of the seal line of the container of the present invention.

Referring now to FIG. 5, a further embodiment of the seal line 230 is illustrated. In this embodiment, the seal line 230 is not substantially Ω shaped as in FIGS. 1, 3, and 4, but rather, defines a rectangular or square shape around the fill port 22. As illustrated, between the two legs 238 and 239, a second seal line 240 can be located dividing the opening 237 into two openings 241 and 243. Of course, if desired, the second seal line 240 need not be provided.

Figure 6:
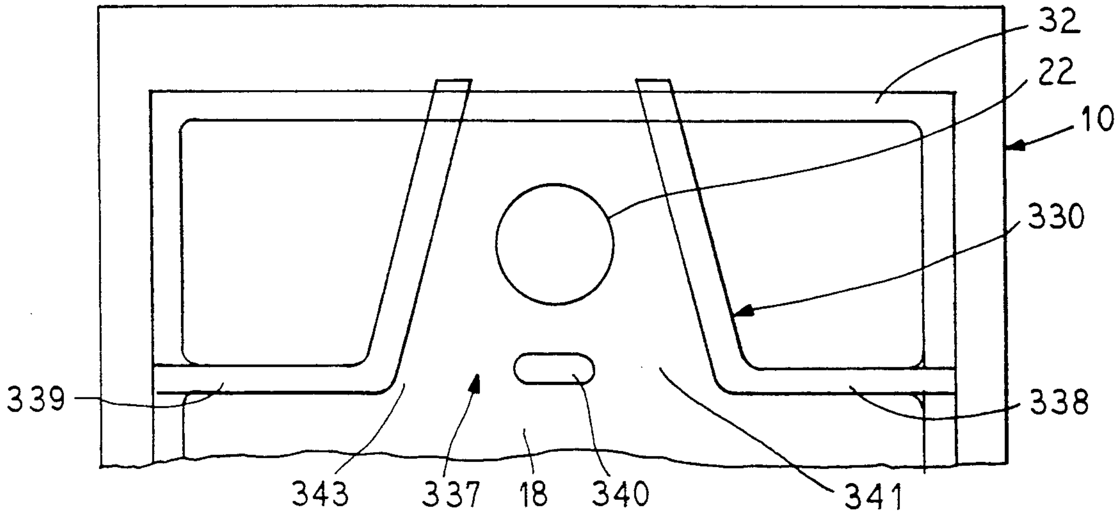
FIG. 6 illustrates a still further embodiment of the seal line of the container of the present invention.

Referring now to FIG. 6, a further embodiment of the seal line 330 is illustrated. In the illustrated embodiment, the legs 338 and 339 extend from the top seal 32 the container 10 initially at an angle. Again, preferably, a second seal line 340 is located within the opening 337 defined by the legs 339 and 338, dividing the opening into two openings 341 and 343.

As disclosed in U.S. Pat. No. 4,840,017, the fill port 22, after the sterile filling and sealing of the port, can be used as a hanger hole. Because of the seal line 30, 130, 230, and 330, stresses are no longer concentrated on the closed-loop seal 26. Therefore, container 10 failures are greatly reduced.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A container for housing a fluid comprising:

a pair of flexible plastic walls, one of the plastic walls defining a front face and one of the plastic walls defining a back face, the plastic walls being secured together around a periphery thereof by a peripheral seal thereby defining an interior;

an access member located at an end of the container for allowing one to access a fluid contained within the interior;

a fill port located on a front face for allowing access to the interior so that the interior can receive a fluid; and the back and front face being sealed along a seal line located within the interior substantially within the peripheral seal, in juxtaposition to the fill port and so constructed and arranged to reduce stress on a seal between the fill port and the back face of the container after the container has received fluid.

2. The container of claim 1 wherein the fill port includes a sealing diaphragm that is ruptured to provide access to the interior of the container.

3. The container of claim 1 wherein the seal line extends from a top of the peripheral seal in two lines to opposite sides of the peripheral seal.

4. The container of claim 1 wherein the peripheral seal line has a substantially Ω shape.

5. The container of claim 1 wherein the seal line is defined, at least in part, by a pair of legs extending from opposite sides of the peripheral seal, the legs defining an opening therebetween allowing fluid to flow from the fill port into a majority of the interior of the container.

6. The container of claim 5 including a further seal line located between the legs and dividing the opening into at least two openings.

7. The container of claim 5 wherein one of the pair of legs has a substantially L shape.

8. The container of claim 1 wherein the seal line is created by heat sealing a portion of the front face to the back face.

9. A container for housing a fluid comprising:

a pair of flexible plastic walls, one of the plastic walls defining a front face and one of said plastic walls defining a back face, the plastic walls being secured together around a periphery thereof by a peripheral seal that defines an interior;

an access member located at an end of the container for allowing one to access a fluid contained within the interior;

a fill port located on a front face for allowing access to the interior so as to allow a fluid to be fed into the interior of the container, the fill port being sealable to the back face to create a circular seal around the fill port after the container receives fluid; and a seal line between the back and front face extending through a portion of the interior and from a top end of the peripheral seal to a first and a second side of the peripheral seal on each side of the fill port and substantially surrounding the circular seal when it is created.

10. The container of claim 9 wherein the fill port includes a sealing diaphragm that is ruptured to provide access to the interior of the container.

11. The container of claim 9 wherein the peripheral seal has a substantially Ω shape.

12. The container of claim 9 wherein the seal line is defined, at least in part, by a pair of legs extending from a top of the peripheral seal, the legs defining an opening therebetween allowing fluid to flow from the fill port into a majority of the interior of the container.

13. The container of claim 12 including a further seal line located between the legs and dividing the opening into at least two openings.

14. The container of claim 9 wherein the seal line is created by heat sealing a portion of the front face to the back face.

15. The container of claim 9 wherein the seal line includes, in part, portions that extend perpendicularly from the top end of the peripheral seal.

16. The container of claim 9 wherein the seal line includes, in part, portions that extend at an angle from the top end of the peripheral seal.

17. The container of claim 9 wherein the seal line includes, in part, portions that extend parallel to the top end of the peripheral seal.

18. A container for housing a fluid comprising:

a pair of flexible plastic walls, one of the plastic walls defining a front face and one of the plastic walls defining a back face, the plastic walls being secured together around a periphery thereof by a peripheral seal thereby defining an interior;

an access member for allowing one to access a fluid contained within the interior;

a fill port located on a front face for allowing access to the interior so that the interior can receive a fluid; and the back and front face being sealed along a seal line located within the interior in juxtaposition to the fill port and so constructed and arranged to reduce stress on a seal between the fill port and the back face of the container after the container has received fluid, the seal line is defined, at least in part, by a pair of legs extending from opposite sides of the peripheral seal, the legs defining at least one opening therebetween.

19. The container of claim 18 wherein the fill port includes a sealing diaphragm that is ruptured to provide access to the interior of the container.

20. The container of claim 18 wherein the peripheral seal line has a substantially Ω shape.

* * * * *